United States Patent [19]
Fell et al.

[11] Patent Number: 5,704,933
[45] Date of Patent: Jan. 6, 1998

[54] ELASTIC STRAP FASTENING SYSTEM WITH BUTTON FASTENERS

[75] Inventors: David Arthur Fell, Neenah; Jeffrey Mark LaFortune; Marianne Keevill Leick, both of Appleton; Lynn Kirkpatrick LeMahieu, Hortonville; Paul Martin Niemi, Neenah, all of Wis.

[73] Assignee: Kimberly-Clark Worldwide, Inc., Neenah, Wis.

[21] Appl. No.: 634,457

[22] Filed: Apr. 18, 1996

[51] Int. Cl.⁶ .................................................. A61F 13/15
[52] U.S. Cl. ........................ 604/399; 604/399; 24/93; 2/265
[58] Field of Search ................... 604/385.1, 385.2, 604/386, 392–3, 396, 398–9; 24/93, 99, 102 FC, 114.3; 2/265, 338, 340

[56] References Cited

U.S. PATENT DOCUMENTS

| | | | |
|---|---|---|---|
| H1440 | 5/1995 | New et al. | 604/386 |
| 1,610,079 | 12/1926 | Duffy . | |
| 1,797,890 | 3/1931 | Wurm . | |
| 1,928,838 | 10/1933 | Marcus | 2/236 |
| 1,963,334 | 6/1934 | Neilson | 2/237 |
| 2,059,103 | 10/1936 | Hardie et al. | 2/237 |
| 3,431,562 | 3/1969 | Souders | 2/221 |
| 3,500,478 | 3/1970 | Foster | 2/221 |
| 3,618,608 | 11/1971 | Brink | 128/287 |
| 3,688,348 | 9/1972 | Klotz et al. | 24/16 |
| 3,708,382 | 1/1973 | Erb | 161/48 |
| 3,745,588 | 7/1973 | Pehle et al. | 2/221 |
| 3,747,171 | 7/1973 | Montague, Jr. | 24/265 |
| 3,848,268 | 11/1974 | D'Ambrosio | 2/237 |
| 3,868,729 | 3/1975 | Lynam | 2/237 |
| 4,047,651 | 9/1977 | McMullen | 224/4 |
| 4,058,853 | 11/1977 | Boxer et al. | 2/239 |
| 4,114,297 | 9/1978 | Famolare, Jr. | 36/50 |
| 4,216,257 | 8/1980 | Schams et al. | 428/93 |
| 4,244,199 | 1/1981 | Rhode | 66/193 |
| 4,291,439 | 9/1981 | Riti | 24/119 |
| 4,294,238 | 10/1981 | Woodford | 128/80 |
| 4,315,508 | 2/1982 | Bokick | 604/392 |
| 4,388,075 | 6/1983 | Mesek et al. | 604/385 |
| 4,416,951 | 11/1983 | Mesnel | 428/586 |
| 4,488,316 | 12/1984 | Mosca | 2/171 |
| 4,500,316 | 2/1985 | Damico | 604/389 |
| 4,549,317 | 10/1985 | D'Ambrosio | 2/237 |
| 4,596,540 | 6/1986 | F'Geppert | 474/253 |
| 4,606,079 | 8/1986 | DeWoskin | 2/338 |
| 4,617,022 | 10/1986 | Pigneul et al. | 604/391 |
| 4,631,932 | 12/1986 | Sommers | 66/192 |
| 4,638,513 | 1/1987 | Woods | 2/268 |
| 4,643,729 | 2/1987 | Laplanche | 604/389 |
| 4,662,037 | 5/1987 | Provost et al. | 24/447 |
| 4,699,823 | 10/1987 | Kellenberger et al. | 428/219 |
| 4,728,326 | 3/1988 | Gilles | 604/392 |

(List continued on next page.)

FOREIGN PATENT DOCUMENTS

| | | |
|---|---|---|
| 0364454B1 | 6/1993 | European Pat. Off. . |
| 0640331A2 | 8/1993 | European Pat. Off. . |
| 1597799 | 9/1981 | United Kingdom . |
| 2185383 | 7/1987 | United Kingdom . |
| 2206506 | 1/1989 | United Kingdom . |
| 2281100 | 2/1996 | United Kingdom . |
| 93/03644 | 3/1993 | WIPO . |
| 95/05140 | 2/1995 | WIPO . |
| 95/20930 | 8/1995 | WIPO . |

*Primary Examiner*—John G. Weiss
*Assistant Examiner*—Ki Yong O
*Attorney, Agent, or Firm*—Thomas M. Gage; Patricia A. Charlier

[57] ABSTRACT

An absorbent article includes a fastening system having first and second buttons bonded to an elastic strap member in respective first and second end regions. The straps are adapted to attach to a garment and maintain the garment in place during use. Reinforcement members are provided within reinforcement zones surrounding the attachment locations of each of the buttons. The reinforcement members locally stabilize the strap member near the attachment locations to minimize or eliminate rolling and twisting of the sides of the strap members during use.

11 Claims, 4 Drawing Sheets

U.S. PATENT DOCUMENTS

| | | | |
|---|---|---|---|
| 4,728,553 | 3/1988 | Daniels | 423/100 |
| 4,770,917 | 9/1988 | Tochacek et al. | 428/95 |
| 4,780,936 | 11/1988 | Brecher | 24/119 |
| 4,787,897 | 11/1988 | Torimae et al. | 604/389 |
| 4,831,997 | 5/1989 | Greene | 124/35 |
| 4,834,820 | 5/1989 | Kondo et al. | 156/73.3 |
| 4,861,322 | 8/1989 | Reddick | 474/254 |
| 4,862,563 | 9/1989 | Flynn | 24/442 |
| 4,870,725 | 10/1989 | Dubowik | 24/442 |
| 4,887,339 | 12/1989 | Bellanger | 24/575 |
| 4,894,060 | 1/1990 | Nestegard | 604/391 |
| 4,904,249 | 2/1990 | Miller et al. | 604/378 |
| 4,909,802 | 3/1990 | Ahr et al. | 604/385.1 |
| 4,931,343 | 6/1990 | Becker et al. | 428/95 |
| 4,932,950 | 6/1990 | Johnson | 604/392 |
| 4,938,754 | 7/1990 | Mesek | 604/385.2 |
| 4,941,237 | 7/1990 | Hovis | 24/304 |
| 4,964,860 | 10/1990 | Gipson et al. | 604/391 |
| 4,970,728 | 11/1990 | D'Ambrosio | 2/237 |
| 4,973,326 | 11/1990 | Wood et al. | 604/391 |
| 4,980,930 | 1/1991 | Cusimano | 2/220 |
| 4,999,853 | 3/1991 | Taner | 2/321 |
| 5,010,595 | 4/1991 | Stradley | 2/227 |
| 5,019,073 | 5/1991 | Roessler et al. | 604/391 |
| 5,049,145 | 9/1991 | Flug | 604/391 |
| 5,053,028 | 10/1991 | Zoia et al. | 604/385.1 |
| 5,077,870 | 1/1992 | Melbye et al. | 24/452 |
| 5,135,522 | 8/1992 | Fahrenkrug et al. | 604/385.1 |
| 5,147,343 | 9/1992 | Kellenberger | 604/368 |
| 5,193,225 | 3/1993 | Karami et al. | 2/312 |
| 5,227,107 | 7/1993 | Dickenson et al. | 264/113 |
| 5,288,546 | 2/1994 | Roessler et al. | 428/284 |
| 5,304,162 | 4/1994 | Kuen | 604/392 |
| 5,325,569 | 7/1994 | Goulait et al. | 24/448 |
| 5,373,587 | 12/1994 | Sexton | 2/237 |
| 5,374,262 | 12/1994 | Keuhn, Jr. et al. | 604/392 |
| 5,386,595 | 2/1995 | Kuen et al. | 2/400 |
| 5,476,702 | 12/1995 | Datta et al. | 428/99 |

ELASTIC STRAP FASTENING SYSTEM WITH BUTTON FASTENERS

BACKGROUND OF THE INVENTION

The present invention relates to an improved button-type fastening system for a garment. More particularly, the invention pertains to a fastening system that includes an elastic strap and button-type fasteners and that enhances product fit and comfort by resisting roping during use. The invention also pertains to absorbent articles incorporating such fastening systems.

Garments such as absorbent articles come in a variety of forms, which is a result of there being so many different types of wearers and use conditions. Each form of garment incorporates a specifically-designed, compatible fastening system. Fastening systems for absorbent articles, by way of illustration, have included adhesive tapes, garment adhesives, and body adhesives; mechanical hook-and-loop type fasteners; button-type fasteners; stretchable side panels; and the like.

Many of these fastening systems have been improved in recent years as a result of their being the continued subject of intense development efforts. In complete contrast, though, is the elastic strap and button fastener fastening system which has received very little attention since its first use until today. This form of fastening system, which is especially common for adult incontinence undergarments, has been a mainstay of the field but until now has not been similarly improved as have other product features. As a result of the improvements in absorbency, gasketing, materials development, and the like, the elastic strap and button fastener fastening system has now become a significant factor in wearer dissatisfaction with fit and comfort of the garment.

Therefore, what is lacking and needed in the art is an improved garment fastening system that utilizes elastic straps and button fasteners and that enhances garment fit and wearer comfort.

SUMMARY OF THE INVENTION

In response to the discussed deficiencies in the prior art, a new fastening system including elastic straps and button fasteners has been developed. The fastening system is suitable for use on garments such as absorbent articles and improves both product fit and wearer comfort.

Evaluation of fastening systems with elastic straps has indicated to Applicants that relatively wider elastic straps improve product fit by reducing sagging of the garment and increasing comfort, security, and leakage protection relative to narrower elastic straps. Applicants also recognized, however, that increased strap width tends to directly increase the degree to which the side edges of the strap tend to roll, twist and rope when the elastic is stretched. This problem is attributable to use of a button or other point-attached fastener, because the lines of force when the elastic strap is stretched tend to be directed toward the attachment location, and the sides of the strap tend to fold about an axis defined by the lines of force.

As can be appreciated, having the side edges of the elastic strap roll and twist can be very uncomfortable and can lead to skin irritation due to localized pressure of the strap. Moreover, rolling of the strap edges can also be detrimental to the fit of the garment and lead to sagging and insecurity. Applicants have discovered that simply increasing the strap tension in an attempt to enhance fit and reduce sagging is not a desirable option, because the higher tensions merely increase the tendency of the strap edges to roll and twist and also decrease wearer comfort by localizing pressure in a small area.

Thus, while Applicants have recognized the benefits to be gained by wider elastic straps, Applicants have also discovered performance characteristics that, in addition to increased product cost, present obstacles to obtaining improved fit and comfort with fastening systems using elastic straps and buttons.

The fastening systems of the present invention overcome the above-referenced obstacles and enable the use of wider elastic straps with button or other point contact fasteners. The fastening systems of the present invention incorporate a reinforcement member bonded to the elastic strap at a position related to the attachment location of the button so that the lines of force created by elongation of the elastic strap do not cause the side edges of the strap to roll and twist. The reinforcement member interrupts the lines of force that would otherwise be directed toward the point of button attachment and cause rolling and twisting upon elongation of the strap. In the present invention, Applicants hypothesize that the forces attributable to elongation are diffused across the reinforcement member instead of being localized toward the point of button attachment.

In one aspect, the present invention concerns a fastening system for use with a garment. The fastening system includes an elastomeric strap member having opposite first and second end edges, opposite side edges extending between the end edges, a first end region contiguous with the first end edge, a second end region contiguous with the second edge, and a central region intermediate and interconnecting the first and second end regions. The fastening system also includes a button bonded to the strap member at an attachment location in the first end region. The button is adapted for releasable attachment to the garment, and means are provided for attaching the second end region of the strap member to the garment. A reinforcement member of the fastening system is bonded to the strap member in a reinforcement zone in the first end region of the strap member. The reinforcement zone represents a portion of the strap member defined within an outer boundary, an inner boundary, and the side edges of the strap member. The outer boundary is located about 12 mm. from the attachment location of the button, toward the first end edge of the strap member. The inner boundary is located about 60 mm. from the attachment location of the button, toward the second end edge of the strap member.

The portion of the strap member that incorporates the reinforcement member desirably has a composite widthwise deflection resistance of at least about 550 grams. This width-wise deflection resistance value, which is described hereinafter in greater detail, characterizes the ability of localized regions of the strap member and reinforcement member composite to resist side edge rolling. More particularly, the portion of the strap member that incorporates the reinforcement member desirably has a composite width-wise deflection resistance of a least 600 grams for improved performance.

In one particular embodiment, first and second buttons are bonded to the elastic strap member at respective first and second attachment locations. In this embodiment, a first reinforcement member is bonded to the strap member in a first reinforcement zone near the first button, and a second reinforcement member is bonded to the strap member in a second reinforcement zone near the second button. Both portions of the strap member that incorporate the reinforcement members have a composite width-wise deflection resistance of at least about 550 grams.

In other embodiments of the invention, the reinforcement member is located at a specific position within the reinforcement zone. For example, the reinforcement member may be bonded to the strap member within about 12 mm. of the attachment location of the button. In one particular embodiment, the reinforcement member is bonded to the strap member, and the button is bonded directly to the reinforcement member, such that the button is disposed on top of the reinforcement member. Alternatively, the reinforcement member may be bonded to the strap member between the attachment location of the button and the central region of a strap member, within about 60 mm. of the attachment location.

In another aspect, the present invention concerns an absorbent article including a garment having first and second waist regions and an intermediate section which interconnects the waist region. The garment, which defines a plurality of button holes in the first and second waist regions, is formed of a liquid-impermeable moisture barrier, and absorbent assembly disposed on the moisture barrier, and a liquid-permeable bodyside liner bonded to the moisture barrier and sandwiching the absorbent assembly between the bodyside liner and the moisture barrier. The absorbent article also includes a pair of elastomeric strap members. Each of the strap members has opposite first and second end edges, opposite side edges extending between the end edges, first and second end regions, and a central region intermediate and interconnecting the end regions. First and second buttons are bonded to each of the strap members at respective first and second attachment locations in the respective first and second end regions. The buttons are adapted for releasable attachment to the button holes. First and second reinforcement members of the absorbent article are bonded to each of the strap members in respective first and second reinforcement zones. The first reinforcement zone includes a portion of each of the strap members defined within a first outer boundary, a first inner boundary, and the side edges of the strap member. The first outer boundary is located about 12 mm. from the first attachment location and toward the first end edge, and the first inner boundary is located about 60 mm. from the first attachment location and toward the second end edge. Correspondingly, the second reinforcement zone includes a portion of each of the strap members defined within a second outer boundary, a second inner boundary, and the side edges of the strap member. The second outer boundary is located about 12 mm. from the second attachment location and toward the second end edge of the strap member. The second inner boundary is located about 60 mm. from the second attachment location and toward the first end edge. The portions of the strap members that incorporate the reinforcement members each have a composite width-wise deflection resistance of at least about 550 grams.

Applicants have discovered that absorbent articles incorporating the present fastening system tend to remain in position better and be more comfortable than current commercial products. The localized stabilization of the elastic straps provided by the reinforcement members minimizes or even eliminates the tendency of the side edges of the straps to roll or twist between the buttons. Consequently, the straps tend to be extremely comfortable. Further, the straps can be placed under greater tensions without tending to rope and twist, and the higher tensions further enhance fit and reduce sagging of the garment. The reinforcement members permit the use of wider strap members, allowing more uniform tension across the entire surface area of the strap member to result in more comfortable straps. Applicants have determined that wearer comfort is enhanced with strap members having a width dimension of at least about 25 mm., and more particularly at least about 30 mm. for improved performance.

Numerous features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DETAILED DESCRIPTION Of THE PREFERRED EMBODIMENTS

Figure 1:
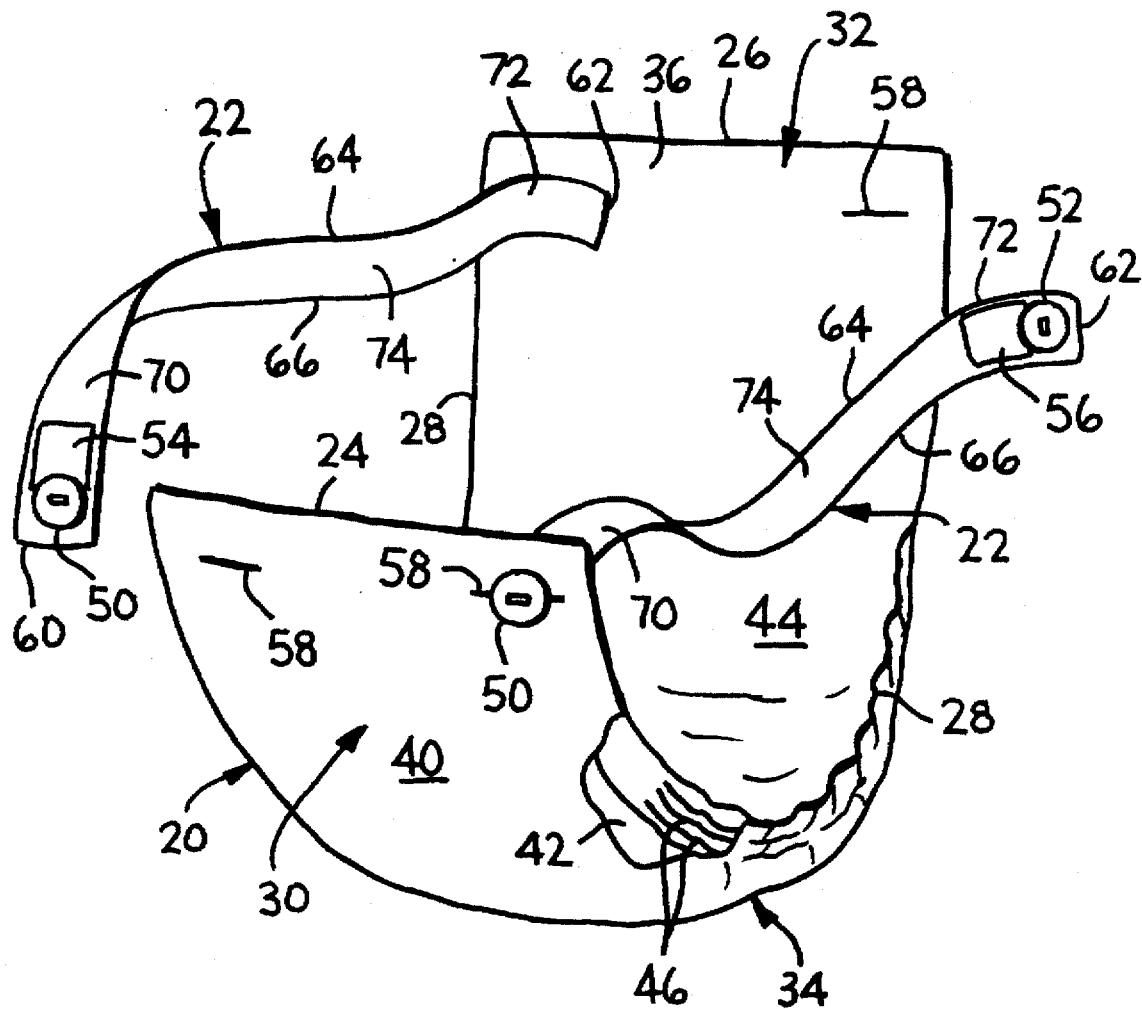
FIG. 1 representatively shows a perspective view of an absorbent article according to the present invention, with portions broken away for purposes of illustration.
Figure 2:
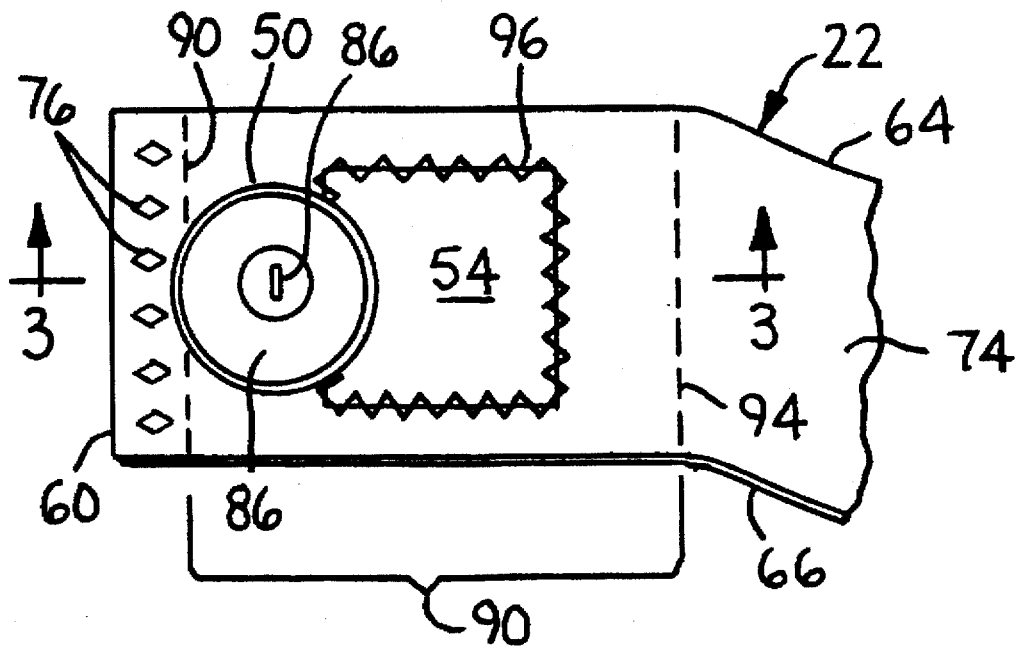
FIG. 2 representatively shows an enlarged perspective view of a portion of one of the two strap members shown in FIG. 1.

With reference to FIGS. 1 and 2, an absorbent article formed according to the invention is shown for purposes of illustration as a disposable undergarment 20 for adult incontinence which is maintained in position about a wearer by a fastening system comprising a pair of strap members 22. As used herein, the term "disposable" includes being disposed of after use and not intended to be washed and reused. The undergarment 20 is shown in FIG. 1 in a relaxed or non-stretched condition, with the strap members 22 only partially attached to the undergarment. The invention may also be embodied in other types of garments, such as other disposable absorbent articles, reusable absorbent articles, or the like.

The illustrated undergarment 20 has opposite, front and back longitudinal end edges 24 and 26, and longitudinal side edges 28 that extend between the longitudinal end edges. The undergarment 20 includes a first or front waist region 30, a second or back waist region 32, and an intermediate, crotch region 34 positioned between and interconnecting the front and back waist regions. The outer edges of the undergarment 20 define a periphery 36 having generally straight end and side edges 24, 26 and 28, although the edges optionally may be curvilinear and contoured.

The front waist region 30 is contiguous with the front end edge 24 and extends longitudinally inward therefrom toward the transverse center line of the undergarment 20. The back waist region 32 is contiguous with the back end edge 26 and extends longitudinally inward therefrom toward the transverse center line. The waist regions 30 and 32 comprise those upper portions of undergarment 20 which, when worn, wholly or partially cover or encircle the waist or mid-lower torso of the wearer. The intermediate, crotch region 34 comprises that portion of undergarment 20 which, when worn, is positioned between the legs of the wearer and covers the lower torso of the wearer. Thus, the crotch region 34 is the area where insults of urine typically occur in the undergarment or other disposable absorbent article.

The undergarment 20 includes a substantially liquid impermeable moisture barrier 40, an absorbent assembly 42 disposed on the moisture barrier, and a substantially liquid permeable bodyside liner 44 bonded to the moisture barrier to sandwich the absorbent assembly therebetween. The moisture barrier 40 and bodyside liner 44 are desirably longer and wider than the absorbent assembly 42 so that the peripheries of the moisture barrier and bodyside liner may be bonded together using ultrasonic bonds, thermal bonds, adhesives, or other suitable means. The peripheries of the moisture barrier 40 and the bodyside liner 44 typically form the side and end margins of the undergarment 20. The absorbent assembly 42 may be bonded directly to the moisture barrier 40 and/or the bodyside liner 44 using ultrasonic bonds, thermal bonds, adhesives, or other suitable means. As used herein, the term "bonded" refers to the joining, adhering, connecting, attaching, or the like, of two elements. Two elements will be considered to be bonded together when they are bonded directly to one another or indirectly to one another, such as when each is directly bonded to intermediate elements. The terms "disposed," "disposed on," "disposed with," "disposed at," "disposed near" and variations thereof are intended to mean that one element can be integral with another element, or that one element can be a separate structure bonded to or placed with or placed near another element.

The moisture barrier 40 desirably comprises a material that is formed or treated to be liquid impermeable. Alternatively, the moisture barrier 40 may comprise a liquid permeable material and other suitable means may be provided to impede liquid movement away from the absorbent assembly, such as a liquid impermeable layer (not shown) associated with the absorbent assembly 42. The moisture barrier 40 may also be gas permeable, such that gases encountered during use of the absorbent garment are able to pass through the material under ordinary use conditions, over either all or part of its surface area.

The moisture barrier 40 may comprise a single layer of material or a laminate of two or more separate layers of material. Suitable moisture barrier materials include films, wovens, nonwovens, laminates of films, wovens, and/or nonwovens, or the like. For example, the moisture barrier 40 may comprise a thin, substantially liquid impermeable web or sheet of plastic film such as polyethylene, polypropylene, polyvinyl chloride or similar material. The moisture barrier material may be transparent or opaque and have an embossed or matte surface. One particular material for the moisture barrier 40 is a polyethylene film that has a nominal thickness of about 0.025 millimeter and a systematic matte embossed pattern, and that has been corona treated on both sides. Another suitable moisture barrier material is an adhesive or thermal laminate comprising a cast or blown film formed of polypropylene, polyethylene or the like, and a spunbond web formed of polypropylene and polyethylene bicomponent fibers in a 50/50 side-by-side configuration.

The absorbent assembly 42 comprises materials adapted to absorb and retain liquid waste. The absorbent assembly 42 may comprise various absorbent materials, such as an airformed batt of cellulosic fibers (i.e., wood pulp fluff) or a coform material composed of a mixture of cellulosic fibers and synthetic polymer fibers. Polymer fibers may be incorporated, for example, in the manner described in U.S. Pat. No. 5,227,107 issued Jul. 13, 1993, to Dickenson et al. The absorbent assembly 42 may also include compounds to increase its absorbency, such as 0–95 weight percent of organic or inorganic high-absorbency materials, which are typically capable of absorbing at least about 15 and desirably more than 25 times their weight in water. Suitable high-absorbency materials are described in U.S. Pat. No. 4,699,823 issued Oct. 13, 1987, to Kellenberger et al. and U.S. Pat. No. 5,147,343 issued Sep. 15, 1992, to Kellenberger, which are incorporated herein by reference. High-absorbency materials are available from various commercial vendors, such as Dow Chemical Company, Hoechst Celanese Corporation, and Allied Colloids, Inc. The absorbent assembly 42 may also include tissue layers or acquisition or distribution layers to help maintain the integrity of fibrous absorbents or transport liquids (not shown).

The bodyside liner 44 is formed of a liquid permeable material so that liquid waste, and possibly semi-solid waste as well, can pass through the liner and be absorbed by the absorbent assembly 42. Suitable bodyside liners 44 may comprise a nonwoven web or sheet of wet strength tissue paper, an apertured film, a spunbonded, meltblown or bonded-carded web composed of synthetic polymer filaments or fibers, such as polypropylene, polyethylene, polyesters or the like, or a web of natural polymer filaments or fibers such as rayon or cotton. In addition, the bodyside liner 44 is desirably nonelastic and may be treated with a surfactant to aid in liquid transfer. In a particular embodiment of the invention, the liner 44 comprises a nonwoven, spunbond polypropylene fabric composed of about 2.8–3.2 denier fibers formed into a web having a basis weight of about 22 gms and density of about 0.06 gm/cc. The fabric is surface treated with about 0.28 weight percent of a surfactant commercially available from Rohm and Haas Co. under the trade designation Triton X-102. As used herein, the term fabric is used to refer to all of the woven, knitted and nonwoven fibrous webs. The term nonwoven web means a web of material which is formed without the aid of a textile weaving or knitting process.

The undergarment 20 is illustrated as having a rectangular periphery 36, but may optionally be hourglass-shaped, I-shaped, T-shaped, or irregularly-shaped. The general shape of the absorbent assembly 42 may correspond to the shape of the undergarment 20 or assume a different shape. For example, the undergarment 20 may include a relatively short absorbent assembly and separate liquid handling layers in the waist regions (not shown) as disclosed in U.S. patent application Ser. No. 08/515,505 titled "Absorbent Article Having Improved Waist Region Dryness And Method Of Manufacture" and filed Aug. 15, 1995, by L. LeMahieu et al. (Attorney Docket No. 12,248) and assigned to the assignee of the present application.

Desirably although not necessarily, the undergarment 20 also includes leg elastic members 46 to draw and hold the side margins of the undergarment 20 against the legs of the wearer and form a seal therewith. The elongated leg elastic members 46 are longitudinally orientated in each side margin (only one side shown in FIG. 1), extending toward the front and back end edges 24 and 26. The leg elastic members 46 are positioned in the illustrated embodiment between the moisture barrier 40 and the bodyside liner 44. Using ultrasonic bonds, adhesives, thermal bonds, or other suitable means, the leg elastic members 46 are attached in a stretched condition to the moisture barrier 40, the bodyside liner 44, or both, in either a straight or a curved shape. Alternatively, the leg elastic members 46 may be attached in a relaxed state to a gathered portion of the moisture barrier 40, the bodyside liner 44, or both.

The leg elastic members 46 may be formed of a dry-spun coalesced multifilament elastomeric thread sold under the tradename LYCRA® and available from E. I. Du Pont de Nemours and Company. Alternately, the elastic members may be formed of other typical elastics utilized in the undergarment-making art, such as a thin ribbon of natural rubber, a stretch bonded laminate material comprising a prestretched elastic meltblown inner layer sandwiched between and bonded to a pair of spunbond polypropylene nonwoven webs, or the like. Elasticity could also be imparted to the absorbent article by extruding a hot melt elastomeric adhesive between the moisture barrier 40 and the liner 44. Other suitable elastic gathering means are disclosed in U.S. Pat. Nos. 4,938,754 to Mesek and 4,388,075 to Mesek et al.

The fastening system in the illustrated embodiment includes a pair of strap members 22 that are raleasably attached to the front and back waist regions 30 and 32 to support the undergarment 20 about the body of the wearer. Attachment systems of this general type are disclosed in U.S. Pat. No. B1 4,315,508 to Bolick, which is incorporated herein by reference. The present fastening system, which is designed to prevent rolling and twisting of the strap 22 during use and thereby enable the use of relatively wide straps if desired, will now be described in greater detail.

Each strap member 22 in the illustrated embodiment is provided with first and second buttons 50 and 52 and first and second reinforcement members 54 and 56. The reinforcement members 54 and 56 stabilize the strap members 22 in localized regions around the buttons 50 and 52 and between the buttons when the strap is elongated during use to prevent rolling and twisting of the straps. The buttons 50 and 52 are adapted to be releasably attached to button holes 58 provided in the undergarment 20. The button holes 58 are desirably formed in the moisture barrier 40 and bodyside liner 44, and may additionally comprise button hole reinforcement tapes (not shown) as is well known in the art. As used herein, the terms "releasably attached," "releasably engaged" and variations thereof refer to two elements being connected or connectable such that the elements tend to remain connected during use absent the wearer applying a unique separation force to one or both of the elements, and the elements being capable of separation without substantial permanent deformation or rupture.

The strap members 22 are each generally rectangular strips of material having opposite, longitudinally spaced first and second end edges 60 and 62, and opposite side edges 64 and 66 extending between the end edges. The strap members 62 are considered for purposes of the present invention as being divided longitudinally into a first end region 70, a second end region 72 and a central region 74 that is intermediate and interconnecting the first and second end regions. The first end region 70 is contiguous with the first end edge 60 and extends longitudinally inward therefrom to the central region 74. The second end region 72 is contiguous with the second end edge 62 and extends longitudinally inward therefrom to the central region 74.

The strap members 22 are formed of an elastomeric material. The terms "elastic," "elasticized" and "elasticity" as used herein refer to that property of a material by virtue of which it tends to recover its original size and shape after removal of a force causing a deformation. The term "elastomeric" refers to a material or composite which can be elongated by at least 25% of its relaxed length and which will recover, upon release of the applied force, at least 10% of its elongation. It is generally preferred that the elastomeric material be capable of being elongated by at least 100%, and more preferably by from 150 to 350%, of its relaxed length and recover, upon release of an applied force, at least 50% of its elongation. The term "force" refers to a physical influence exerted by one body on another which produces acceleration of bodies that are free to move and deformation of bodies that are not free to move. In one particular embodiment, the strap member 22 comprises a woven-knitted fabric formed using nylon and polyester strands, which is available from Shelby Elastics, Inc. of Shelby, N.C., under the trade designation NP96 or NP50.

The size of the strap members 22 will vary depending on the type of garment to which they are attached and the size of the intended wearers. Each strap member 22 suitably has a width dimension defined between the opposite side edges 64 and 66 of at least about 25 mm., and more particularly at least about 30 mm. for improved performance. The strap members 22 have a longer length dimension defined between the opposite end edges 60 and 62 that is suitably from about 15 to about 40 cm. In one particular embodiment, each strap member 22 has a length dimension of 29.8 cm. and a width dimension of 38 mm. The cut ends of the strap members 22 may be bonded by ultrasonic bonds 76 as illustrated in FIG. 2, or be bonded by adhesives or other suitable means to prevent raveling.

Figure 3:
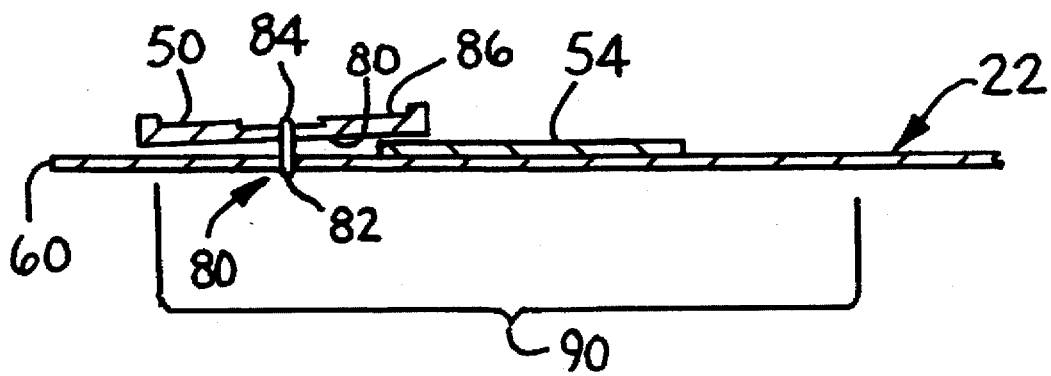
FIG. 3 representatively shows an enlarged section view taken generally from the plane of the line 3—3 in FIG. 2.

FIG. 3 represents an enlarged section view taken generally from a plane of line 3—3 in FIG. 2, but taken slightly off center to illustrate attachments of the buttons 50 and 52. While FIGS. 2 and 3 depict only one end of a strap member 22, it should be understood that the opposite end can be constructed in a similar manner. The first and second buttons 50 and 52 are bonded to the respective first and second end regions 70 and 72 of each strap member 22 at an attachment location 80 (FIG. 3). The attachment location 80 is defined by the location at which a thread 82 or other suitable means bonds the button 50 or 52 to the strap member 22. The thread 82 is illustrated as passing through sewing holes 84 in the buttons 50 and 52 and passing through the strap member 22 although membrane buttons with holes formed during attachment are also suitable.

In the illustrated embodiment, the buttons 50 and 52 have an upper, contoured surface 86 and an opposite, generally flat lower surface 88. Buttons 50 and 52 suitable for use with the present invention may be formed of polypropylene and have a diameter of 22 mm., such as those available from Engineering Industries of Verona, Wis., and identified as a green membrane button. In the illustrated embodiment, both end regions 70 and 72 of each strap member 22 may be attached to the undergarment 20 with the buttons 50 or 52. Alternatively, however, one end of each strap member 22 could be formed integral with the undergarment 20 or bonded thereto by other suitable means (not shown).

The term "button" is used herein to refer to a group of fasteners that can be attached to the strap members 22 at a point or an otherwise relatively small region in relation to the width dimension of the strap member. Examples of such fasteners include buttons, snaps, hook eyes, or the like. More particularly, such fasteners have an attachment location constituting less than about 40 percent of the width dimension of the strap member 22, and more particularly less than about 30 percent of the width dimension of the strap member.

Applicants have determined that these fasteners share a common problem, which is that when the elastic strap member 22 is elongated, lines of force are formed within the strap member that are directed at a gradual angle from the side edges 64 and 66 of the strap longitudinally outward and transversely inward toward the attachment location 80 of the fastener. In essence, the strap member 22 "necks down" near the attachment location 80. When the strap member 22 is positioned against the body of the wearer, the side edges 64 and 66 of the strap member tend to fold about an axis defined by the lines of force. As noted previously, these folded sides would represent an irritant to the wearer because the strap forces would be concentrated in a smaller area, and they would also adversely impact the fit of the undergarment. The present invention concerns the recognition of this problem and the use and placement of the reinforcement members 54 and 56 to provide improved elastic strap members with button fasteners.

The first and second reinforcement members 54 and 56 are bonded to the respective first and second end regions 70 and 72 of each strap member 22 at locations that are at least partially in areas of the strap member referred to as first and second reinforcement zones 90 (FIGS. 2 and 3). Each reinforcement zone 90, which is described in greater detail hereinafter, represents an area of the strap member 22 that is particularly effective for placement of a reinforcement member 54 or 56. In the embodiment illustrated in FIGS. 1–3, each reinforcement member 54 and 56 is bonded directly to this strap member 22 with the lower surface 88 of each button 50 and 52 partially overlapping the surface of the reinforcement member.

The reinforcement members 54 and 56 comprise relatively thin materials which when bonded to the strap member 22 provide a greater composite stiffness than that of the strap member 22 alone. In particular embodiments, the reinforcement member material alone has a greater stiffness than the strap member material alone. The relative stiffnesses of the reinforcement members 54 and 56 and the strap members 22 may be determined by a variety of known methods, for example a comparison of the Gurley stiffness values for the individual materials. Suitable materials for use as the reinforcement members 54 and 56 may include plastic, wood, fabrics coated with a heat sealable thermoplastic adhesive, woven materials such as cloth belting material, or the like. Alternatively, a thermoplastic polymer or non-tacky adhesive resin may be extruded or otherwise applied onto the strap member (not shown). One fabric material suitable for the reinforcement members 54 and 56 is a permanent form belt backing with polypropylene filled belting available from E Z International of Saddle Brook, N.J., and referred to as white belt backing. Another suitable material is a label material having a thickness of 0.076 mm. available from Electro Seal Corp. of Pompton Lakes, N.J., under the trade designation RT-130. The reinforcement members 54 and 56 may also comprise a molded hook material available from Velcro Industries B. V., Amsterdam, Netherlands, or affiliates thereof.

Applicants have recognized that selection of suitable reinforcement members 54 and 56 and localized placement of the reinforcement members in areas of each strap member 22 referred to herein as the reinforcement zones 90 minimizes or in some instances eliminates rolling of the side edges 64 and 66 of the straps. Each reinforcement zone 90 can be viewed as a area of the strap member 22 surrounding the attachment location 80 of one of the buttons 50 and 52. The longitudinal extent of each reinforcement zone 90 is defined by an outer boundary 92 and an inner boundary 94 while the width-wise extent of each reinforcement zone is defined by the side edges 64 and 66 of the strap member 22.

For purposes of illustration, the outer and inner boundaries 92 and 94 are shown in FIG. 2 as dashed lines. Applicants have determined that the reinforcement members 54 and 56 remain effective to reduce strap rolling and twisting at different distances from the button attachment locations 80 depending on whether the reinforcement member is located between or outside the buttons 50 and 52, which explains the different locations of the outer and inner boundaries 92 and 94. The outer boundary 92 of the first reinforcement zone 90 is located about 12 mm. from the first attachment location 80 and disposed between the first attachment location and the first end edge 60. The first inner boundary 94 of the first reinforcement zone 90 is located about 60 mm. from the first attachment location 80 and disposed between the first attachment location and the second end edge 62.

Although the second reinforcement zone 90 which corresponds to the second end region 72 of the strap member 22 is not shown in FIGS. 2 and 3, it should be clear that the outer boundary 92 of the second reinforcement zone 90 is located about 12 mm. from the second attachment location 80 and disposed between the second attachment location and the second end edge 24. Also, the second inner boundary 94 of the second reinforcement zone 90 is located about 60 mm. from the second attachment location 80 and disposed between the second attachment location and the first end edge 60.

Applicants have determined that placement of a suitable reinforcement member 54 or 56 within the reinforcement zone 90 prevents substantial force vectors from being directed from the side edges 64 and 66 at a gradual angle toward the attachment locations 80 of the buttons 50 and 52. By interrupting these inwardly-directed force vectors, the tendency of the side edges of the strap members 22 to roll and twist is greatly reduced or eliminated. In contrast, placement of a reinforcement member outside the reinforcement zone has been found to have minimal effect in preventing the strap member from rolling and twisting along the sides.

In the embodiment illustrated in FIGS. 1–3, the reinforcement members 54 and 56 are located between the attachment locations 80 of the buttons 50 and 52 and the center of region 74 of each strap member 22. More particularly, each reinforcement member 54 and 56 is disposed entirely between an attachment location 80 and an inner boundary 94 of the reinforcement zone 90.

Figure 4:
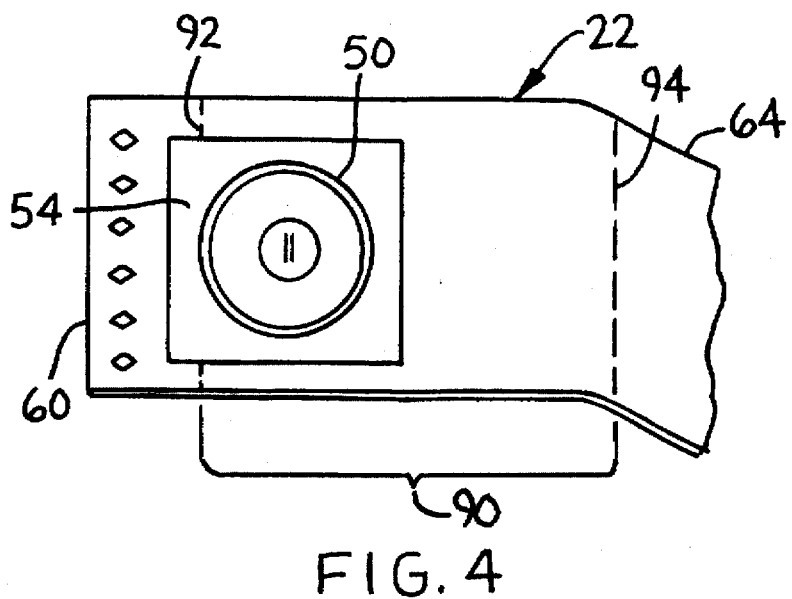
FIG. 4 representatively shows a perspective view similar to FIG. 2, but illustrating another embodiment of the invention.
Figure 5:
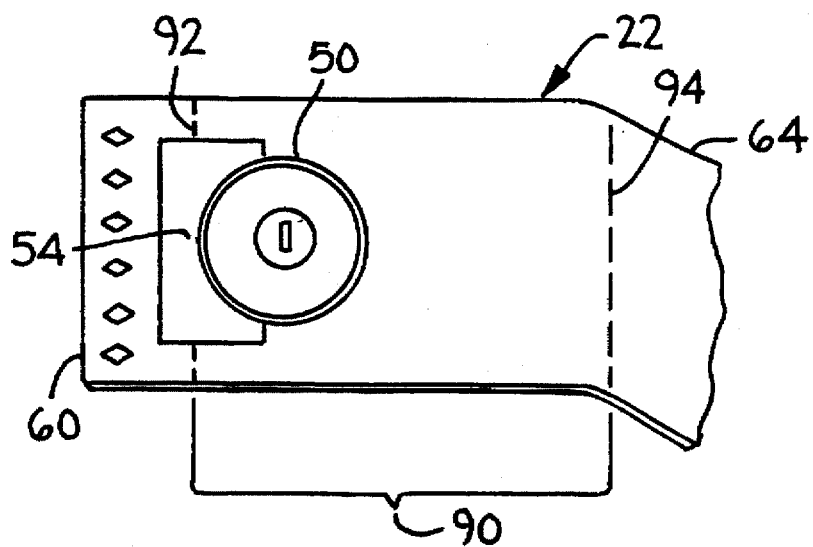
FIG. 5 representatively shows a perspective view similar to FIG. 2, but illustrating an additional embodiment of the invention.

Alternative locations of the reinforcement members 54 and 56 are illustrated in FIGS. 4 and 5, where components similar to those previously described have been given the same reference numeral. With particular regard to FIG. 4, the buttons 50 and 52 (only one shown) are bonded directly to the reinforcement members 54 and 56, which are in turn bonded directly to the strap members 22. As a result, the reinforcement members 54 and 56 are disposed between the strap member 22 and the buttons 50 and 52, and at least partially within the reinforcement zones 90. Alternatively, the reinforcement members 54 and 56 could be disposed on the side of the strap members 22 that is remote from the buttons 50 and 52 or comprise multiple pieces bonded on both sides of the strap member (not shown). Attachment of the buttons 50 and 52 on top of the reinforcement members 54 and 56 as illustrated in FIG. 4 may reduce somewhat the ease of which the buttons can be inserted into the button holes 58, however, this may be offset by modifying the button or attachment to increase slightly the distance between the button and the strap members 22.

In the embodiment illustrated in FIG. 5, the reinforcement members 54 and 56 (only one shown) are bonded to the strap members 22 between the attachment locations 80 of the buttons 50 and 52 and the respective end edges 60 and 62 of the strap members. More particularly, at least portions of the reinforcement members 54 and 56 are disposed between the attachment locations 80 of the buttons 50 and 52 and the outer boundaries 92 of the reinforcement zones 90. In the illustrated embodiments, the reinforcement members 54 and 56 are disposed completely within the bounds of the reinforcement zones 90. In preferred embodiments of the invention, the reinforcement members 54 and 56 are disposed sufficiently close to the attachment locations 80 of the buttons 50 and 52 so as to be positioned at least partly between the lower surface 88 of the button and the strap members 22.

The size of the reinforcement members 54 and 56 is desirably selected to minimize or prevent the sides of the strap members 22 from rolling over and also to avoid contact with the skin of the wearer. As a result, the width-wise dimension of the reinforcement members 54 and 56, which extends in the direction between the side edges 64 and 66 of the strap members 22, is suitably from about 50 to 100 percent of the width dimension of the strap members. In addition, the width-wise dimension of the reinforcement members 54 and 56 is such that the reinforcement members are recessed inward from the side edges 64 and 66 by from about 4 to about 10 mm., for improved performance. By spacing the reinforcement members 54 and 56 inward from the side edges 64 and 66 of the strap members 22, the likelihood of irritation caused by the reinforcement members rubbing the skin of the wearer is reduced. The length-wise dimension of the reinforcement members 54 and 56, measured parallel to the length dimension of the strap members 22, is selected to provide adequate stabilization of the strap members 22 and is believed to be related to the stiffness of the reinforcement member and the location of the reinforcement member within the reinforcement zone 90. In one particular embodiment of the invention, the strap members 22 have a width dimension of 38.1 mm., and the reinforcement members 54 and 56 have a width-wise dimension of 31.8 mm. and a length-wise dimension of 25.4 mm.

The reinforcement members 54 and 56 may be bonded to the strap members 22 by one or more methods including sewing, extrusion application, adhesives, heat lamination, rotary or plunge ultrasonic bonding, or the like. The attachment method must be sufficient to prevent the reinforcement members 54 and 56 from detaching from the strap member 22 when the strap is elongated. Further, the attachment method is selected and carried out to avoid creating points of irritation on the surface of the strap member 22 that faces the wearer during use. It is also desirable for the attachment method to withstand multiple washing and drying cycles, for example about 10, because the strap members 22 are frequently maintained and reused with multiple garments.

In the embodiment illustrated in FIGS. 2 and 3, the reinforcement members 54 and 56 are sewn in place by stitches 96 around at least a portion of the periphery of each reinforcement member. The reinforcement members 54 and 56 may additionally or alternatively be bonded to the strap members 22 over part or all of the surface area of the reinforcement members, for example with adhesives or ultrasonic bonds. The selection of a particular bonding method may depend in part on the materials selected for the strap members 22 and the reinforcement members 54 and 56.

In the embodiment illustrated in FIG. 4, the buttons 50 and 52 can be bonded directly to both the reinforcement members 54 and 56 and the strap members 22. Alternatively, the buttons 50 and 52 could be bonded directly to only the reinforcement members 54 and 56 and the reinforcement members in turn bonded directly to the strap members. In one particular embodiment, the reinforcement members 54 and 56 comprise a molded hook material, and the hooks are embedded into the strap members 22 to facilitate attachment of the reinforcement members to the strap members.

Figure 6:
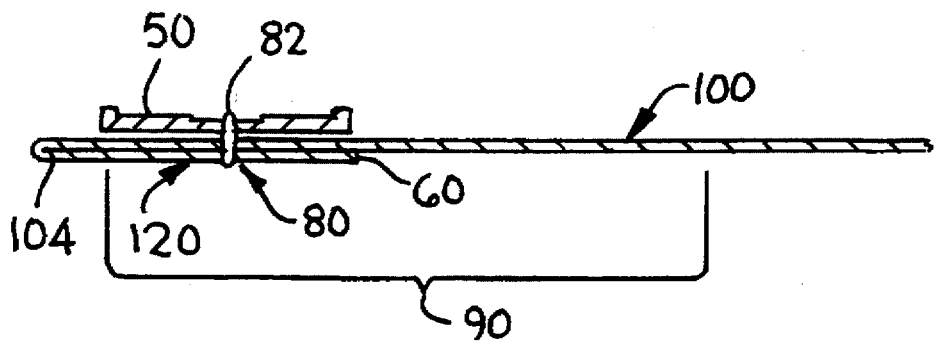
FIG. 6 representatively shows a section view similar to FIG. 3, but illustrating a further embodiment of the invention.
Figure 7:
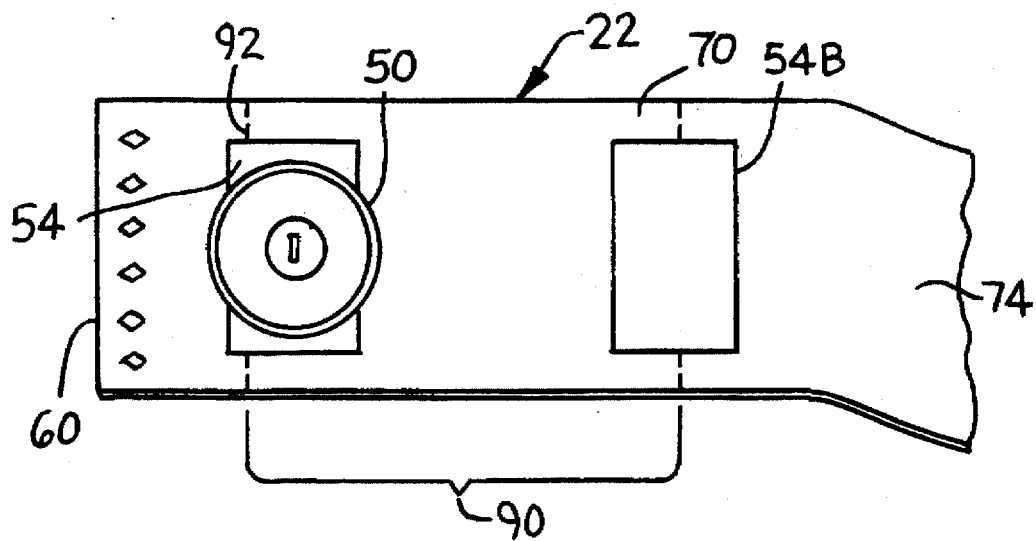
FIG. 7 representatively shows a perspective view similar to FIG. 2, but illustrating a still further embodiment of the invention.

Additional embodiments of the invention are illustrated in FIGS. 6 and 7. With reference first to FIG. 6, a strap member 100 includes opposite longitudinal end edges 60 and 62 (only one shown) and folded portions 102 contiguous with the longitudinal end edges. Each folded portion 102 is folded back onto the strap member 100 about fold line 104 to form a dual thickness portion of the strap member. In this way, the folded portions 102 form integral reinforcement members to provide localized stabilization of the strap member 22 near the attachment locations 80 of the buttons 50 and 52 (only one shown). Similar to the previously-described embodiments, the folded portions 102 are located within reinforcement zones 90 having outer and inner boundaries 92 and 94.

In the embodiment illustrated in FIG. 7, each of the first and second end regions 70 and 72 of each strap member 22 includes a pair of reinforcement members 54A and 54B or 56A and 56B (only one pair shown). In this embodiment, the first reinforcement member 54A of each pair may be disposed between a button 50 or 52 and the strap member 22. The second reinforcement member 54B of the pair may be disposed between the first reinforcement member 54A and the central region 74 of the strap member 22. Both reinforcement members 54A and 54B of the pair are at least partially and desirably completely located within each reinforcement zone 90. In particular embodiments, the first and second reinforcement members of 54A and 54B of each pair are separated by a distance of less than about 60 mm., and particularly by less than about 50 mm. for improved performance.

In one aspect of the invention, the portions of each strap member 22 that incorporate the reinforcement members 54 and 56 have a composite width-wise deflection resistance of at least about 550 grams, more particularly at least about 600 grams, for improved performance. The composite width-wise deflection resistance measures the amount of resistance to bending that is provided by a composite specimen including a portion of the strap member and at least a portion of the reinforcement member 54 or 56. In the embodiment illustrated in FIG. 6, these composite width-wise deflection resistance values are desirably provided by a composite specimen including at least a portion of the dual thickness region of the strap member 100. Composite width-wise deflection resistance has been found to be a useful characterization of the width-wise or transverse stability of the composite. A suitable procedure for determining composite width-wise deflection resistance is set forth in greater detail hereinafter.

In use, the undergarment 20 is positioned on the body of the wearer and secured in position using the fastening system. The wearer can engage one button 50 or 52 of each strap member 22 with a button hole 58 in the back waist region 32. After stretching or relaxing the strap members 22 to obtain the desired tension therein, the wearer can then engage the opposite button 50 or 52 of each strap member with one of the corresponding button holes 58 in the front waist region 30. During application of the strap members 22 and during use, the reinforcement members 54 and 56 provide localized, width-wise stabilization of the strap members 22 near and between the buttons 50 and 52. In this way, force vectors within the strap member 22 which would otherwise be formed at an angle from the side edges 64 and 66 toward the attachment locations 80 of the buttons 50 and 52 are prevented from forming. The propensity of the side edges of the strap members 22 to roll and twist is thereby minimized or eliminated.

Each of the foregoing or similar embodiments of the invention may be constructed by providing each of the individual components and bonding them together in the manner set forth above. The material for the strap members 22, the material for the reinforcement members 54 and 56, the location of the reinforcement members, and the means for attaching the reinforcement members to the strap members may all be selected and adjusted as necessary to provide the requisite composite width-wise deflection resistance values referenced above.

Having thus described the present invention and the process for making it, a number of examples were prepared to give a more detailed understanding of the invention. These examples and the test procedures for measuring them are set forth below. The particular amounts, proportions, compositions and parameters are meant to be exemplary, and are not intended to specifically limit the scope of the invention.

TEST PROCEDURES

The composite width-wise deflection resistance test measures the peak load as a test specimen taken from a strap member 22 is deflected about an axis parallel to the longitudinal or length dimension of the strap member. The test employs a Sintech material test system, also know as a tensile tester. An appropriate test system is the Model 1/S available from MTS Systems Corporation of Eden Prairie, Minn. The material test system is provided with an appropriately sized load cell, for example, a 4.54 kgm. (10 lb.) load cell available from MTS Systems Corporation. The material test system is operated using suitable control software, for example, TEST WORKS® version 3.03 for WINDOWS® available from MTS Systems Corporation.

Figure 8:
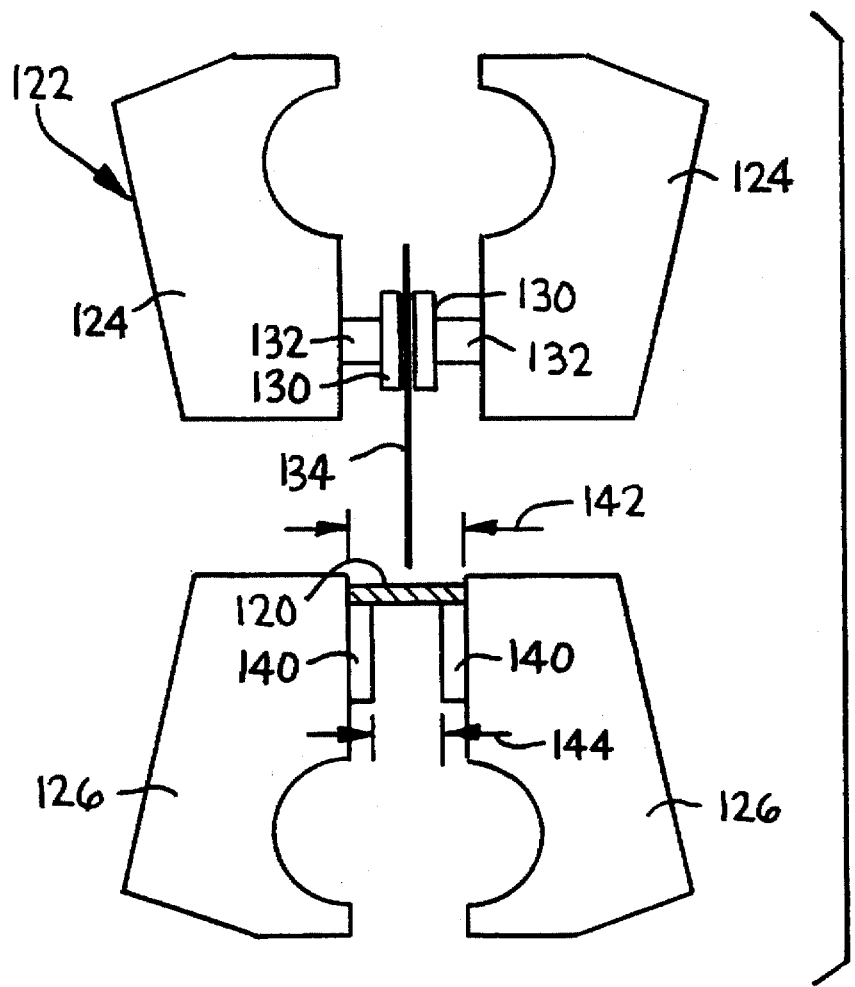
FIG. 8 representatively shows a front plan view of a test apparatus for determining a composite width-wise deflection resistance value for a specimen taken from one of the two strap members shown in FIG. 1.

With reference to FIG. 8, a test specimen 120 is illustrated in proper position for testing in the material test system 122. The material test system 122 includes upper and lower pneumatic grips 124 and 126 that are vertically movable relative to one another. The upper pneumatic grips 124 include an opposed pair of rubber-coated grip facings 130. The grip facings 130 are adapted to move toward one another through the action of pneumatic cylinders 132. As illustrated, a rigid metal plate 134 is held in place as a result of being pressed between the grip facings 130. The metal plate measures 105 mm. in length, 80 mm. in width, and 1 mm. in thickness. The metal plate 134 is positioned so that the width dimension of the plate is parallel to the direction of movement of the upper and lower pneumatic grips 124 and 126.

The lower pneumatic grips 126 include an opposed pair of rubber-coated grip facings 140. The grip facings 140 of the lower pneumatic grips 126 are controlled by pneumatic cylinders (not shown) that are maintained in a retracted position for this test. The spacing between the two halves of the lower pneumatic grips 126 is illustrated by arrow 142 and is maintained at 21 mm. The distance between the grip facings 140 of the lower pneumatic grips 126 is illustrated by arrow 144 and is maintained at 11 mm.

The test specimen 120 is cut from the strap member 22 using a scissors or the like, in the following manner. The width of the test specimen 120 is 21 mm. and is measured parallel to the width-wise dimension of the strap member 22. The 21 mm. width of the test specimen 120 is thus cut from the middle of the strap member 22, centered between the side edges 64 and 66. The length dimension of the test specimen 120 is taken from the portion of the strap member 122 that includes a reinforcement member 154 or 156. The length of the test specimen 120 corresponds to the length of the reinforcement member 54 or 56, except that the minimum length is 25.4 mm. and the maximum length is 38.1 mm. Any buttons 50 or 52 that am bonded to the test specimen 120 am removed with a scissors or knife prior to testing.

The composite width-wise deflection resistance test is begun by calibrating and preparing the equipment as specified by the manufacturer. The test specimen 120 is positioned in the lower pneumatic grips 126 with the reinforcement member 54 or 56 disposed toward the metal plate 134. The test specimen 120 is oriented such that the 21 mm. width dimension is perpendicular to the plane of the metal plate 134. The edges of the test specimen 120 are allowed to rest on the top surfaces of the grip facings 140 of the lower pneumatic grips 126.

During the test, the lower pneumatic grips 126 are maintained stationary while the upper pneumatic grips 124 are moved vertically relative thereto. The metal plate 134 is squared as much as possible relative to the test specimen 120 and lowered until the metal plate almost touches the test specimen. At this time, the control software is initiated. In general, the upper pneumatic grips 124 are lowered at a rate of 5.08 cm. per minute to a distance of 2 cm. and then returned to their original position. The peak load measured by the load cell is recorded and represents the composite width-wise deflection resistance value for that test specimen 120. The control software program is reprinted below. For purposes of clarity, inactive Result Calculation lines have been omitted.

is 38.1 mm. Any buttons 50 or 52 that are bonded to the test specimen 120 are removed with a scissors or knife prior to testing.

The composite width-wise deflection resistance test is begun by calibrating and preparing the equipment as specified by the manufacturer. The test specimen 120 is positioned in the lower pneumatic grips 126 with the reinforcement member 54 or 56 disposed toward the metal plate 134. The test specimen 120 is oriented such that the 21mm. width dimension is perpendicular to the plane of the metal plate 134. The edges of the test specimen 120 are allowed to rest on the top surfaces of the grip facings 140 of the lower pneumatic grips 126.

During the test, the lower pneumatic grips 126 are maintained stationary while the upper pneumatic grips 124 are moved vertically relative thereto. The metal plate 134 is squared as much as possible relative to the test specimen 120 and lowered until the metal plate almost touches the test specimen. At this time, the control software is initiated. In general, the upper pneumatic grips 124 are lowered at a rate of 5.08 cm. per minute to a distance of 2 cm. and then returned to their original position. The peak load measured by the load cell is recorded and represents the composite width-wise deflection resistance value for that test specimen 120. The control software program is reprinted below. For purposes of clarity, inactive Result Calculation lines have been omitted.

```
                Start of Test Message 1
                Start of Test Message 2
                Start of Test Message 3
                Start of Test Message 4

Pre-Sample Messages:
                Pre-Sample Message #1
                Pre-Sample Message #2
                Pre-Sample Message #3

Pre-Specimen Messages:
                Pre-Specimen Message #1
                Pre-Specimen Message #2
                Pre-Specimen Message #3

Graphics Window, Y-Axis:
                Y Axis Scaling Max    MANUAL
                Y Axis Scaling Min    MANUAL
                Y-Axis Label          LOAD
                Y-Axis units          Gm
                Y-Axis Min            0.000000
                Y-Axis Max            10000.000000
                Decimals              1

                Graphics Window, X-Axis:
                X Axis Scaling Max    MANUAL
                X Axis Scaling Min    MANUAL
                X-Axis label          EXTENSION
                X-Axis units          mm
                X-Axis Min            0.000000
                X-Axis Max            20.000000
                Decimals              1
                X Offset              0.000000
```

22

Test Flow:

| | |
|---|---|
| Method Access Level | [9] |
| Specimens per Sample | [999] |
| Speed Increment | [0.100000] |
| Show Graph | [Y] |
| Show Results | [Y] |
| Take Data During Pause | [N] |
| Auto Sample Increment | [N] |
| Auto Raw Data Save | [N] |
| Auto Reject on Limits | [N] |
| Auto Sample Print | [N] |
| Discard on Reject | [Y] |
| Auto Comment | [N] |
| Auto Sample Upload | [N] |
| Auto Crosshead Return | [N] |
| Gage Removal | [N] |
| Pause for Gage Removal | [N] |

Reference Name:

Reference Loaded: NONE

Configuration:

| | |
|---|---|
| Load Direction | DOWN |
| Extension Direction | DOWN |
| Compliance | No |
| End Of Test Action | STOP |
| Method Type | STANDARD |

Move Segments:

| | |
|---|---|
| Type | RESET EXTENSION |
| Status | ENABLE |
| Direction | NO CHANGE |
| Aquisition | INACTIVE |

23

|    |              |                                  |
|----|--------------|----------------------------------|
|    | Data Points  | 0                                |
|    | End Action   | CONTINUE                         |
|    | Message      |                                  |
| | Type         | TARE STRAIN 1                    |
|    | Status       | DISABLE                          |
|    | Direction    | NO CHANGE                        |
|    | Aquisition   | INACTIVE                         |
|    | Data Points  | 0                                |
| | End Action   | CONTINUE                         |
|    | Message      |                                  |
|    | Type         | TARE STRAIN 2                    |
|    | Status       | DISABLE                          |
| | Direction    | NO CHANGE                        |
|    | Aquisition   | INACTIVE                         |
|    | Data Points  | 0                                |
|    | End Action   | CONTINUE                         |
|    | Message      |                                  |
| 20 |              |                                  |
|    | Type         | GO TO STRAIN @ CONSTANT SPEED    |
|    | Status       | ENABLE                           |
|    | Direction    | DOWN                             |
|    | Aquisition   | ACTIVE                           |
| | Data Points  | 500                              |
|    | End Action   | CONTINUE                         |
|    | Message      | Initial Speed to %strain point   |
|    | Type         | GO TO STRAIN @ CONSTANT SPEED    |
| | Status       | ENABLE                           |
|    | Direction    | DOWN                             |
|    | Aquisition   | ACTIVE                           |
|    | Data Points  | 499                              |
|    | End Action   | CONTINUE                         |
| | Message      | Secondary Speed to %strain point |

Sample Inputs:

| # | Label | Default | Attribute |
|---|---|---|---|
| 0 | User Input 1 | User Default 1 | OPTIONAL |
| 1 | User Input 2 | User Default 2 | OPTIONAL |
| 2 | User Input 3 | User Default 3 | OPTIONAL |
| 3 | User Input 4 | User Default 4 | OPTIONAL |
| 4 | User Input 5 | User Default 5 | OPTIONAL |
| 5 | User Input 6 | User Default 6 | OPTIONAL |
| 6 | User Input 7 | User Default 7 | OPTIONAL |
| 7 | User Input 8 | User Default 8 | OPTIONAL |
| 8 | User Input 9 | User Default 9 | OPTIONAL |
| 9 | User Input 10 | User Default 10 | OPTIONAL |

Sample Naming Format:

| Alias | Sample ID | Length = | 30 |
|---|---|---|---|
| Alias | | Length = | 0 |
| Alias | | Length = | 0 |
| Alias | | Length = | 0 |
| Alias | | Length = | 0 |

Channel Mapping:

| # | Label | Units Class | Status | Formula | |
|---|---|---|---|---|---|
| [0] | EXTENSION | DIMENSION | ACTIVE | P0 | (Primary Strain) |
| [1] | TIME | TIME | ACTIVE | P1 | |
| [2] | LOAD | LOAD | ACTIVE | P2 | |
| [3] | LOGICAL 3 | DIMENSION | INACTIVE | P3 | (Secondary Strain) |
| [4] | LOGICAL 4 | LOAD | INACTIVE | P4 | |

Report Header:

Strap Stiff

Compression Load (g)

Built In Reports:

|    | Built-In Report #0 | | | Built-In 1 | | |
|----|--------------------|---|---|------------|---|---|
|    | Print Header | | | Y | | |
|    | Print Sample Info | | | Y | | |
|    | Print Individual Specimens | | | Y | | |
| | Print Stats | | | N | | |
|    | Print Calc Inputs | | | Y | | |
|    | Print Test Inputs | | | Y | | |
|    | Print Comments | | | N | | |
|    | | | | | | |
| | Built-In Report #1 | | | Built-In 2 | | |
|    | Print Header | | | Y | | |
|    | Print Sample Info | | | Y | | |
|    | Print Individual Specimens | | | Y | | |
|    | Print Stats | | | Y | | |
| | Print Calc Inputs | | | Y | | |
|    | Print Test Inputs | | | Y | | |
|    | Print Comments | | | Y | | |

Display Units:

|    |           |        |
|----|-----------|--------|
| | Load      | Lb     |
|    | Extension | In     |
|    | Speed     | In/Min |
|    | Area      | Sq.In  |
|    | Strain    | %      |
| | Time      | Min    |
|    | Stress    | PSI    |

Specimen Inputs:

|    | # | Label | Units | Default | Attribute | Panel Input | Reference |
|----|---|-------|-------|---------|-----------|-------------|-----------|
| | 0 | Diameter | In | 0.500 | HIDDEN | N | |
|    | 1 | Length | In | 0.125 | HIDDEN | N | |
|    | 2 | Height | In | 2.00 | HIDDEN | N | Rslt 10,21 |
|    | 3 | Area | Sq.In | 2.00 | HIDDEN | N | |
|    | 4 | Misc.Input 1 | (none) | 1.00 | HIDDEN | N | |

| # | Label | Units | Default | Attribute | Panel Input | Reference |
|---|---|---|---|---|---|---|
| 5 | Misc.Input 2 (none) | | 1.00 | HIDDEN | N | |
| 6 | Misc.Input 3 (none) | | 1.00 | HIDDEN | N | |
| 7 | Misc.Input 4 (none) | | 1.00 | HIDDEN | N | |

Calculation Inputs:

| # | Label | Units | Default | Attribute | Panel Input | Reference |
|---|---|---|---|---|---|---|
| 0 | Gage Length | In | 2.00 | DISPLAY | N | Req. 2,2,3,9 |
| 1 | Bonded Gage | In/In | 1.00 | OPTIONAL | N | |
| 2 | Removal Point | In | 1.00 | OPTIONAL | N | |
| 3 | Brk % Drop | % | 10.0 | OPTIONAL | N | Req 3 |
| 4 | Brk Drop Elong | In | 0.001 | OPTIONAL | N | |
| 5 | Brk Load Value | Lb | 50.00 | OPTIONAL | N | |
| 6 | Yield Angle | deg | 0.00 | OPTIONAL | N | |
| 7 | Yield % SegLen | % | 10.00 | OPTIONAL | N | |
| 8 | Slope Tol. | % | 98.00 | OPTIONAL | N | |
| 9 | Slope % Seglen | % | 10.00 | OPTIONAL | N | |
| 10 | Min Slope Load | Lb | 0.00 | OPTIONAL | N | |
| 11 | Max Slope Load | Lb | 10000.00 | OPTIONAL | N | |
| 12 | Slope Min Strss | PSI | 0.00 | OPTIONAL | N | |
| 13 | Slope Max Strss | PSI | 1000.00 | OPTIONAL | N | |
| 14 | %Strain Point1 | % | 2.00 | OPTIONAL | N | Rslt 27,29,31,33,35 |
| 15 | %Strain Point2 | % | 5.00 | OPTIONAL | N | Rslt 28,30,32,34,36 |
| 16 | Elong Point1 | In | 0.10 | OPTIONAL | N | Rslt 23,25 |
| 17 | Elong Point2 | In | 0.10 | OPTIONAL | N | Rslt 24,26 |
| 18 | Stress Point1 | PSI | 100.0 | OPTIONAL | N | Rslt 37,39 |
| 19 | Stress Point2 | PSI | 200.0 | OPTIONAL | N | Rslt 38,40 |
| 20 | Yield Offset | % | 2 | OPTIONAL | N | Rslt 16,17,18,19,20,21 |
| 21 | Slack Pre-Load | Lb | 5.00 | OPTIONAL | N | |
| 22 | %Strain Point3 | % | 5.00 | OPTIONAL | N | Rslt 46 |

Test Inputs:

| # | Label | Units | Default | Attribute | Panel Input | Reference |
|---|---|---|---|---|---|---|
| 0 | Inital Speed | In/Min | 2.00 | DISPLAY | N | MSeg 3 |
| 1 | Secondary Speed | In/Min | 4.00 | OPTIONAL | N | MSeg 4 |

| # | Category | Unit | Value | Type | | |
|---|---|---|---|---|---|---|
| 2 | % Strain Limit | % | 100.0 | OPTIONAL | N | MSeg 3 |
| 3 | Deformation Lim | % | 200.0 | OPTIONAL | N | MSeg 4 |
| 4 | Load Limit HI | Lb | 25 | DISPLAY | N | |
| 5 | Load Limit LO | Lb | -5000 | OPTIONAL | N | |
| 6 | Ext Limit HI | mm | 20.0 | DISPLAY | N | |
| 7 | Ext Lmit LO | In | -20.0 | OPTIONAL | N | |
| 8 | Strain Limit HI | % | 3000000.1 | OPTIONAL | N | |
| 9 | Strain Limit LO | % | -300000.0 | OPTIONAL | N | |
| 10 | Stress Limit HI | PSI | 2999999.9 | OPTIONAL | N | |
| 11 | Stress Limit LO | PSI | -3000000 | OPTIONAL | N | |
| 12 | # Cycles | (none) | 20.0 | OPTIONAL | N | |
| 13 | Time Limit | Sec | 10000 | OPTIONAL | N | |
| 14 | Brk Sensitivity | % | 75 | OPTIONAL | N | |
| 15 | RETURN Point | In | 0.0 | DISPLAY | N | |

Required Markers

| # | Category | Code | Attribute |
|---|---|---|---|
| 1 | BREAK POINT | F | MOVABLE |
| 2 | YIELD POINT | Y | MOVABLE |
| 3 | MODULUS BEGIN | B | MOVABLE |
| 4 | MODULUS END | M | MOVABLE |

Optional Markers

| # | Category | Code | Attribute | Formula | Inputs | Reference |
|---|---|---|---|---|---|---|
| 5 | AT MIDPOINT | 0 | HIDDEN | | | |
| 6 | AT PIP | 1 | HIDDEN | | | |
| 7 | AT PIP | 2 | HIDDEN | | | |
| 8 | AT PIP | 3 | HIDDEN | | | |
| 9 | AT PIP | 4 | HIDDEN | | | |
| 10 | FREE | 5 | HIDDEN | @INDEX(LOAD,PEAK) | | |
| 11 | FREE | 6 | HIDDEN | @INDEX(LOAD,PEAK) | | |
| 12 | FREE | 7 | HIDDEN | @INDEX(LOAD,PEAK) | | |
| 13 | FREE | 8 | HIDDEN | @INDEX(LOAD,PEAK) | | |
| 14 | FREE | 9 | HIDDEN | @INDEX(LOAD,PEAK) | | |

Required Calculations

| # | Category | Procedure | Inputs |
|---|---|---|---|
| 0 | AREA | INACTIVE | |
| 1 | STRESS | 1/AREA | |
| 2 | PRIMARY STRAIN | 1/C00 | C00 |
| 3 | SECONDARY STRAIN | 1/C00 | C03 |
| 4 | BREAK | INACTIVE | |
| 5 | YIELD POINT | INACTIVE | |
| 6 | PRIMARY SLOPE | INACTIVE | |
| 7 | SLACK COMPENSATION | INACTIVE | |
| 8 | OFFSET YIELD | INACTIVE | |
| 9 | GAGE LENGTH ADJUSTMENT | INACTIVE | C00 |

Result Calculations

| # | Label | Category | Formula | Units | Attribute |
|---|---|---|---|---|---|
| 0 | Peak Load | FIXED | PEAKLOAD | Gm | DISPLAY |

Upload and Sample Reports:

| | |
|---|---|
| Free Form Sample Report | Fixed Report (1) |
| Free Form Upload Report | <None> |
| Upload Destination | COMM PORT |
| Upload Filename | DATA.TMP |

Test Page Windows:

| | |
|---|---|
| Show Load Meter | Y |
| Show Extension Meter | Y |
| Show Strain1 Meter | N |
| Show Strain2 Meter | N |
| Show Machine Status | N |
| Show Test Messages | N |
| Show Specimen Inputs | N |
| Show Description | N |
| Show Panel | N |

29

| | | |
|---|---|---|
| | Show Machine | Y |
| | Show Multi-Display | N |
| | Show Handset | Y |
| | Show Ruler | N |
| | Show Peaks | N |

Ruler Defaults:

| | | |
|---|---|---|
| | Ruler Maximum Up | 40.000000 |
| | Ruler Maximum down | -40.000000 |
| | Ruler Control Mode | POSITION |
| | Ruler Units | In |
| | Ruler Gage Length | 1.000000 |
| | Ruler Gage Length Units | In |
| | Ruler Decimals Precision | 1 |
| | | |

Meter Defaults:

| | | |
|---|---|---|
| | Load Meter Full Scale | 100.000000 |
| | Load Meter Units | Lb |
| | Load Meter Decimals | 1 |
| | Load Meter Mode | DIGITAL |
| | Extension Meter Full Scale | 1.000000 |
| | Extension Meter Units | In |
| | Extension Meter Decimals | 1 |
| | Extension Meter Mode | DIGITAL |
| | Strain1 Meter Full Scale | 1.000000 |
| | Strain1 Meter Units | In |
| | Strain1 Meter Decimals | 1 |
| | Strain1 Meter Mode | ANALOG |
| | Strain2 Meter Full Scale | 1.000000 |
| | Strain2 Meter Units | In |
| | Strain2 Meter Decimals | 1 |
| | Strain2 Meter Mode | ANALOG |

Peaks Defaults:

| | | |
|---|---|---|
| | Show Load Peak | Y |
| | Load Units | Lb |
| | Load Decimals | 1 |
| | Show Extension Peak | Y |
| | Extension Units | In |
| | Extension Desimals | 1 |
| | Show Strain Peak | Y |
| | Strain Units | % |
| | Strain Desimals | 1 |
| | Show Stress Peak | Y |
| | Strain Units | PSI |
| | Strain Desimals | 1 |
| | Show Cycle Count | Y |
| | Panel End Action Defaults: | |
| | Load End Action | STOP |
| | Extension End Action | STOP |
| | Strain End Action | STOP |
| | Stress End Action | STOP |
| | | |

EXAMPLES

EXAMPLES

In each of the following examples, pairs of strap members for use with disposable absorbent undergarments were produced. Each strap member was formed of an elastomeric material comprising nylon, polyester and elastic materials and had a length of about 27.3 cm. and a width of about 38.1 mm. The elastomeric material was purchased from Shelby Elastics of Shelby, N.C. and identified as NP 50. The strap ends were cut to length using scissors and the cut ends were ultrasonically bonded as shown in FIG. 2 to prevent raveling. Buttons were sewn onto the opposite end regions of the strap members with the button centers spaced apart by 24.1 cm. In each example, the distance from the center of the button attachment to the nearest end edge of the strap member was 16 mm. In all instances, the buttons and the reinforcement structures were centered in the widthwise direction of the strap member. The buttons, which measured 22 mm. in diameter, were purchased from Engineering Industries under the tradename green membrane buttons.

Example 1

In each end region, each strap member of Example 1 included a reinforcement region that consisted of a concentrated ultrasonic bond pattern formed in the strap member. Each reinforcement region measured 38.1 mm. in width which corresponded to the full strap width and 12.7 mm. in length. The buttons were attached to the strap members in the center of the reinforcement regions.

The composite width-wise deflection resistance of 4 test specimens from these strap members were measured and found to have an average value of 199.6 grams, with a standard deviation of 20.2 grams. The test specimens had a width of 21 mm. and a length of 25.4 mm.

Example 2

In each end region, each strap member of Example 2 included a reinforcement region that consisted of a concentrated ultrasonic bond pattern formed in the strap member. Each reinforcement region measured 38.1 mm. in width and 12.7 mm. in length. The buttons were positioned between each reinforcement region and the nearest end edge, with the closest part of each reinforcement region being spaced 20.5 mm. from the attachment location of the corresponding button.

The composite width-wise deflection resistance values for Example 2 strap members were not separately measured because the structure of the reinforcement regions is a replica of those in Example 1.

Example 3

In each end region, each strap member of Example 3 included first and second reinforcement regions that consisted of concentrated ultrasonic bond patterns formed in the strap member. Each reinforcement region measured 38.1 mm. in width and 12.7 mm. in length. The buttons were attached to the strap members in the center of the first reinforcement regions. The closest part of each second reinforcement region was spaced 50.8 mm. from the attachment location of the corresponding button.

The composite width-wise deflection resistance values for Example 3 strap members were not separately measured because of the first and second reinforcement regions are each replicas of those in Example 1 and they are spaced apart from one another so that they would comprise separate test specimens.

Example 4

In each end region, each strap member of Example 4 included first, second and third reinforcement regions that consisted of concentrated zig-zag stitch patterns formed in the strap member using all purpose, dual duty plus cotton covered polyester thread. Each reinforcement region measured approximately 38.1 mm. in width and 4 mm. in length, and there was a 12.7 mm. gap between the reinforcement regions. The buttons were attached to the strap members in the center of the first reinforcement regions. The second and third reinforcement regions were positioned inward of the first reinforcement regions.

The composite width-wise deflection resistance of 8 test specimens from these strap members were measured and found to have an average value of 241.0 grams, with a standard deviation of 3.9 grams. The test specimens had a width of 21 mm. and a length of 25.4 mm., with each test specimen including only one of the first, second, or third reinforcement regions.

Example 5

In each end region, each strap member of Example 5 included a reinforcement member ultrasonically bonded to the strap member. Each reinforcement member consisted of a single-sided, uni-directional hook material available from Velcro Industries and identified as HTH-840 with 22 Series hooks. The hooks were pressed into the strap material prior to ultrasonic bonding. Each reinforcement member measured 31.8 mm. in width and 8.0 mm. in length. The buttons were attached to the strap members through the center of the reinforcement members.

The composite width-wise deflection resistance of 8 test specimens from these strap members were measured and found to have an average value of 452.4 grams, with a standard deviation of 35.7 grams. The test specimens had a width of 21 mm. and a length of 25.4 mm.

Example 6

In each end region, each strap member of Example 6 included a reinforcement member sewn on to the strap member. Each reinforcement member consisted of a belting material available from E Z International, and identified as white belt backing. Each reinforcement member measured 31.8 mm. in width and 8.0 mm. in length. The buttons were attached to the strap members through the center of the reinforcement members.

The composite width-wise deflection resistance of 5 test specimens from these strap members were measured and found to have an average value of 654.4 grams, with a standard deviation of 23.2 grams. The test specimens had a width of 21 mm. and a length of 25.4 mm.

Example 7

In each end region, each strap member of Example 7 included first and second reinforcement members sewn on to the strap member. Each reinforcement member consisted of a belting material available from E Z International, and identified as white belt backing, and measured 31.8 mm. in width and 8.0 mm. in length. The buttons were attached to the strap members through the center of the first reinforcement members. The closest part of each second reinforcement member was spaced 50.8 mm. from the attachment location of the corresponding button.

The composite width-wise deflection resistance values for Example 7 strap members were not separately measured because the first and second reinforcement members are each replicas of those in Example 6 and they are spaced apart from one another so that they would comprise separate test specimens.

Example 8

In each end region, each strap member of Example 8 included first and second reinforcement members sewn on to the strap member. Each reinforcement member consisted of a belting material available from E Z International, and identified as white belt backing, and measured 31.8 mm. in width and 8.0 mm. in length. The first and second reinforcement members were bonded at corresponding locations on opposite sides of the strap member. The buttons were attached to the strap members through the center of both the first and the second reinforcement members.

The composite width-wise deflection resistance of 5 test specimens from these strap members were measured and found to have an average value of 1526.2 grams, with a standard deviation of 355.1 grams. The test specimens had a width of 21 mm. and a length of 25.4 mm.

Example 9

In each end region, each strap member of Example 9 included a reinforcement member sewn on to the strap member. Each reinforcement member consisted of a belting material available from E Z International, and identified as white belt backing. Each reinforcement member measured 31.8 mm. in width and 25.4 mm. in length. The buttons were attached to the strap members through the center of the reinforcement members.

The composite width-wise deflection resistance of 8 test specimens from these strap members were measured and found to have an average value of 1424.2 grams, with a standard deviation of 56.4 grams. The test specimens had a width of 21 mm. and a length of 25.4 mm.

Example 10

In each end region, each strap member of Example 10 included a reinforcement member sewn on to the strap member. Each reinforcement member consisted of a belting material available from E Z International, and identified as white belt backing. Each reinforcement member measured 31.8 mm. in width and 38.1 mm. in length. The buttons were attached to the strap members through the reinforcement members in an off-center arrangement so that the outer edge of each reinforcement member was located 12.7 mm. from the point of button attachment.

The composite width-wise deflection resistance of 5 test specimens from these strap members were measured and found to have an average value of 2480.2 grams, with a standard deviation of 79.2 grams. The test specimens had a width of 21 mm. and a length of 38.1 mm.

Example 11

In each end region, each strap member of Example 11 included first and second reinforcement members sewn on to the strap member. Each reinforcement member consisted of a belting material available from E Z International, and identified as white belt backing, and measured 31.8 mm. in width and 25.4 mm. in length. The first and second reinforcement members were bonded at corresponding locations on opposite sides of the strap member. The buttons were attached to the strap members through the center of both the first and second reinforcement members.

The composite width-wise deflection resistance of 8 test specimens from these strap members were measured and found to have an average value of 3982.8 grams, with a standard deviation of 34.1 grams. The test specimens had a width of 21 mm. and a length of 25.4 mm.

Example 12

Each end region of the strap members of Example 12 included a folded portion contiguous with the end edge. The folded portion had a length of 25.4 mm. and the resulting dual-layer portion of the strap member was sewn together. The buttons were attached to the strap members through the resulting dual-layer portion.

The composite width-wise deflection resistance of 8 test specimens from these strap members were measured and found to have an average value of 589.0 grams, with a standard deviation of 22.8 grams. The test specimens had a width of 21 mm. and a length of 25.4 mm.

Example 13

In each end region, each strap member of Example 13 included a reinforcement member sewn on to the strap member. Each reinforcement member consisted of a belting material available from E Z International, and identified as white belt backing, and measured 31.8 mm. in width and 25.4 mm. in length. The buttons were positioned between each reinforcement member and the nearest end edge, with the closest part of each reinforcement region being spaced 17.4 mm. from the attachment location of the corresponding button.

The composite width-wise deflection resistance values for Example 13 were not separately measured because the structure of the reinforcement regions is a replica of those in Example 9.

Each of the strap members from Examples 1 through 13 were tested in combination with a disposable absorbent undergarment. The undergarment comprised a liquid impermeable moisture barrier, a spunbond polypropylene bodyside liner bonded to the moisture barrier, and an absorbent assembly sandwiched between the moisture barrier and the bodyside liner. The moisture barrier comprised an adhesive laminate of a polyethylene film inner layer and a spunbond nonwoven outer layer. The bodyside liner, absorbent assembly and moisture barrier were bonded together using a construction adhesive. The undergarment also included leg elastic members secured along the two side margins of the garment. Button holes with reinforcement tapes were provided generally in the four corners of the undergarment.

A fit study was conducted using 15 panelists having hip sizes in the range of 121.3 to 149.9 cm. and waist sizes in the range of 95.3 to 135.3 cm. Applicants hypothesized that relatively large individuals would stress the suspension system most and would therefore be able to best differentiate reinforcement functionality. Each panelist tested each of the Example 1 through 13 strap members. Each panelist was advised to wear an undergarment with one pair of Example strap members overnight and return the next day for photographs and evaluations.

Test results are summarized in Table 1 below. The coded test results are based on photographs of the undergarments and strap members taken during the test. Code A indicates that the strap members remained relatively flat and did not twist or roll. Code B indicates that the strap members exhibited a relatively small amount of twisting and rolling. Code C indicates that the strap members twisted and rolled.

The column Deflection Resistance Avg. (grams) shows the average composite width-wise deflection resistance value for the Example strap member, or that of the replica structures as described above.

TABLE 1

Deflection Resistance

| Example No. | Avg. (grams) | Test Code |
| --- | --- | --- |
| 1 | 199.6 | C |
| 2 | 199.6 | C |
| 3 | 199.6 | C |
| 4 | 241.0 | C |
| 5 | 452.4 | C |
| 6 | 654.4 | B |
| 7 | 654.4 | B |
| 8 | 1526.2 | B |
| 9 | 1424.2 | A |
| 10 | 2480.2 | A |
| 11 | 3962.8 | A |
| 12 | 589.0 | B |
| 13 | 1424.2 | A |

From the data presented in Table 1, it is evident that strap members according to the present invention as claimed hereinafter are capable of reducing or eliminating twisting and rolling during use. Applicants hypothesize that proper placement of a reinforcement region or member in the described reinforcement zones near the button in combination with the appropriate degree of cross direction stiffness of the strap member as measured by the composite width-wise deflection resistance test described herein will result in a better fitting and more comfortable suspension system for garments.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, two named components could represent portions of the same structure. Therefore, the invention should not be limited by the specific embodiments described, but only by the claims.

We claim:

1. A fastening system for use with a garment, the fastening system comprising:

an elastomeric strap member having opposite first and second end edges, opposite side edges extending between the end edges, a first end region contiguous with the first end edge, a second end region contiguous with the second end edge, and a central region intermediate and interconnecting the first and second end regions;

a button bonded to the strap member at an attachment location in the first end region, the button adapted for releasable attachment to the garment;

means for attaching the second end region to the garment; and a reinforcement member bonded to the strap member in a reinforcement zone in the first end region, the reinforcement member bonded at a position related to the attachment location of the button which interrupts lines of force that would otherwise be directed toward the point of button attachment which causes rolling and twisting upon elongation of the strap, the reinforcement zone comprising a portion of the strap member defined within an outer boundary, an inner boundary, and the side edges, the outer boundary located about 12 millimeters from the attachment location toward the first end edge, and inner boundary located about 60 millimeters from the attachment location toward the second end edge;

wherein a portion of the strap member incorporating the reinforcement member has a composite width-wise deflection resistance of at least about 550 grams.

2. The fastening system of claim 1 wherein the strap member has a strap width defined between the side edges of at least about 30 millimeters.

3. A fastening system for use with a garment, the fastening system comprising:

an elastomeric strap member having opposite first and second end edges, opposite side edges extending between the end edges, a first end region contiguous with the first end edge, a second end region contiguous with the second end edge, and a central region intermediate and interconnecting the first and second end regions;

a button bonded to the strap member at an attachment location in the first end region, the button adapted for releasable attachment to the garment;

means for attaching the second end region to the garment; and a reinforcement member bonded to the strap member in a reinforcement zone located within about 12 millimeters of the attachment location, the reinforcement member bonded at a position related to the attachment location of the button which interrupts lines of force that would otherwise be directed toward the point of button attachment which causes rolling and twisting upon elongation of the strap;

wherein a portion of the strap member incorporating the reinforcement member has a composite width-wise deflection resistance of at least about 550 grams.

4. A fastening system for use with a garment, the fastening system comprising:

an elastomeric strap member having opposite first and second end edges, opposite side edges extending between the end edges, a first end region contiguous with the first end edge, a second end region contiguous with the second end edge, and a central region intermediate and interconnecting the first and second end regions;

a button bonded to the strap member at an attachment location in the first end region, the button adapted for releasable attachment to the garment;

means for attaching the second end region to the garment; and a reinforcement member bonded to the strap member in a reinforcement zone located between the attachment location and the central region and within about 60 millimeters of the attachment location, the reinforcement member bonded at a position related to the attachment location of the button which interrupts lines of force that would otherwise be directed toward the point of button attachment which causes rolling and twisting upon elongation of the strap;

wherein a portion of the strap member incorporating the reinforcement member has a composite width-wise deflection resistance of at least about 550 grams.

5. A fastening system for use with a garment, the fastening system comprising:

an elastomeric strap member having opposite first and second end edges, opposite side edges extending between the end edges, a first end region contiguous with the first end edge, a second end region contiguous with the second end edge, and a central region intermediate and interconnecting the first and second end regions;

a reinforcement member bonded to the strap member;

a button bonded directly to the reinforcement member such that the reinforcement member interrupts lines of force that would otherwise be directed toward the point of button attachment which caused rolling and twisting upon elongation of the strap, the button adapted for releasable attachment to the garment;

means for attaching the second end region to the garment; and wherein a portion of the strap member incorporating the reinforcement member has a composite width-wise deflection resistance of at least about 550 grams.

6. The fastening system of claim 1, 3, 4 or 5, wherein the reinforcement member comprises a belting material.

7. The fastening system of claim 1, 3. 4 or 5, wherein the reinforcement member comprises a thermoplastic polymer.

8. The fastening system of claim 1, 3, 4, or 5, wherein the reinforcement member is disposed completely within the reinforcement zone.

9. The fastening system of claim 1, 3, 4 or 5, wherein the reinforcement member is recessed inward from the side edges.

10. An absorbent article, comprising:

a garment having first and second waist regions, an intermediate section which interconnects the waist regions, the garment defining a plurality of button holes in the first and second waist regions, the garment comprising a liquid-impermeable moisture barrier, an absorbent assembly disposed on the moisture barrier, and a liquid-permeable bodyside liner bonded to the moisture barrier and sandwiching the absorbent assembly between the bodyside liner and the moisture barrier;

a pair of elastomeric strap members, each of the strap members having opposite first and second end edges, opposite side edges extending between the end edges, a first end region contiguous with the first end edge, a second end region contiguous with the second end edge, and a central region intermediate and interconnecting the first and second end regions;

first and second buttons bonded to each of the strap members at respective first and second attachment locations in the respective first and second end regions, the buttons adapted for releasable attachment to fie button holes; and first and second reinforcement members bonded to each of the strap members in respective first and second reinforcement zones, the first reinforcement zone comprising a portion of each of the strap members defined within a first outer boundary, a first inner boundary, and the side edges, the first outer boundary located about 12 millimeters from the first attachment location toward the first end edge, and the first inner boundary located about 60 millimeters from the first attachment location toward the second end edge, the second reinforcement zone comprising a portion of each of the strap members defined within a second outer boundary, a second inner boundary, and the side edges, the second outer boundary located about 12 millimeters from the second attachment location toward the second end edge, and the second inner boundary located about 60 millimeters from the second attachment location toward the first end edge;

wherein first and second portions of each strap member that incorporate the respective first and second reinforcement members each have a composite width-wise deflection resistance of at least about 550 grams that the reinforcement member interrupts lines of force that would otherwise be directed toward the point of button attachment which causes rolling and twisting upon elongation of the strap.

11. A fastening system for use with a garment, the fastening system comprising:

an elastomeric strap member having opposite first and second end edges, opposite side edges extending between the end edges, a first end region contiguous with the first end edge, a second end region contiguous with the second end edge, and a central region intermediate and interconnecting the first and second end regions, the first end region comprising a folded portion contiguous with the first end edge that is folded about a fold line to form a dual thickness portion of the strap member;

a button bonded to the dual thickness portion of the strap member such that the dual thickness portion interrupts lines of force that would otherwise be directed toward the point of button attachment which causes rolling and twisting upon elongation of the strap, the button adapted for releasable attachment to the garment; and means for attaching the second end region to the garment;

wherein a portion of the strap member incorporating the dual thickness has a composite width-wise deflection resistance of at least about 550 grams.

* * * * *